United States Patent [19]

Forse et al.

[11] Patent Number: 5,762,935
[45] Date of Patent: Jun. 9, 1998

[54] ANTI-INFLAMMATORY AND INFECTION PROTECTIVE EFFECTS OF SESAMIN-BASED LIGNANS

[75] Inventors: R. Armour Forse, Brookline; Sambasiva Chavali, Boston, both of Mass.

[73] Assignee: Beth Israel Deaconess Medical Center, Inc., Boston, Mass.

[21] Appl. No.: 429,014

[22] Filed: Apr. 26, 1995

Related U.S. Application Data

[63] Continuation of Ser. No. 201,682, Feb. 25, 1994.
[51] Int. Cl.$^6$ ..................................... A61K 35/78
[52] U.S. Cl. ............... 424/195.1; 514/469; 514/783; 514/885
[58] Field of Search ..................... 426/804, 810; 514/464, 468, 783, 825, 886, 887, 904, 905; 424/195.1, DIG. 13

[56] References Cited

U.S. PATENT DOCUMENTS

| | | | |
|---|---|---|---|
| 3,901,875 | 8/1975 | Park | 424/195.1 |
| 3,920,440 | 11/1975 | Takaoka et al. | 71/88 |
| 4,317,816 | 3/1982 | Arichi et al. | 424/195.1 |
| 4,339,442 | 7/1982 | Takemoto et al. | 536/4.1 |
| 4,375,480 | 3/1983 | Soma | 514/844 |
| 4,427,694 | 1/1984 | Benecke et al. | 424/195.1 |
| 4,442,092 | 4/1984 | McBrayer | 424/195.1 |
| 4,501,734 | 2/1985 | Tanaka et al. | 424/195.1 |
| 4,649,206 | 3/1987 | Namiki et al. | 549/435 |
| 4,708,820 | 11/1987 | Namiki et al. | 426/542 |
| 4,722,941 | 2/1988 | Eckert et al. | 514/784 |
| 4,752,618 | 6/1988 | Mascioli et al. | 514/560 |
| 4,755,504 | 7/1988 | Liu | 514/26 |
| 4,767,626 | 8/1988 | Cheng | 424/195.1 |
| 4,774,229 | 9/1988 | Jordan | 514/25 |
| 4,774,343 | 9/1988 | Namiki et al. | 549/435 |
| 4,780,475 | 10/1988 | Cerra et al. | 514/561 |
| 4,803,153 | 2/1989 | Shibata et al. | 435/2 |
| 4,810,726 | 3/1989 | Bistrian et al. | 514/943 |
| 4,920,098 | 4/1990 | Cotter et al. | 514/23 |
| 4,966,893 | 10/1990 | Pang et al. | 514/54 |
| 4,981,844 | 1/1991 | Alexander et al. | 514/21 |
| 5,053,387 | 10/1991 | Alexander | 514/21 |
| 5,055,446 | 10/1991 | Alexander et al. | 514/23 |
| 5,089,268 | 2/1992 | Katz | 424/450 |
| 5,166,139 | 11/1992 | Bombardelli et al. | 514/26 |
| 5,180,588 | 1/1993 | Shinmen et al. | 424/439 |
| 5,209,826 | 5/1993 | Ozaki et al. | 435/134 |
| 5,211,953 | 5/1993 | Shinmen et al. | 424/439 |
| 5,214,062 | 5/1993 | Mark et al. | 514/560 |
| 5,229,136 | 7/1993 | Mark et al. | 424/195.1 |
| 5,231,085 | 7/1993 | Alexander et al. | 514/44 |
| 5,260,336 | 11/1993 | Forse et al. | 514/560 |
| 5,270,335 | 12/1993 | Akimoto et al. | 514/470 |
| 5,273,965 | 12/1993 | Kensil et al. | 514/3 |
| 5,397,778 | 3/1995 | Forse et al. | 514/198 |

FOREIGN PATENT DOCUMENTS

| | | |
|---|---|---|
| 0 387 000 | 9/1990 | European Pat. Off. |
| 0 409 654 | 1/1991 | European Pat. Off. |
| 0 519 673 | 12/1992 | European Pat. Off. |
| 02138120 | 5/1990 | Japan |
| 03027319 | 2/1991 | Japan |
| 04368326 | 12/1992 | Japan |

OTHER PUBLICATIONS

"Active Oxygen Eliminating Element". Unexamined Japanese Patent Application No. 6–227977 by Suntory Ltd., *Patent Abstracts of Japan* 18(601):115C–1274.

Darias, V. et al. (1990) "Cytostatic and Antibacterial Activity of Some Compounds Isolated from Several Lamiaceae Species from the Canary Islands" *Planta Medica* 56(1):70–72.

Hirose, N. et al. (1992) "Suppressive Effect of Sesamin against 7,12–Dimethylbenz[a]-anthracene Induced Rat Mammary Carcinogenesis", *Anticancer Research* 12(4):1259–1266.

"Lipoxygenase Inhibitor", Unexamined Japanese Patent Application No. 2–138120 by Nippon Kayaku Co. Ltd., *Patent Abstracts of Japan* 14(377):45 C–748.

Sugano, M. and K. Akimoto "Sesamin: A Multifunctional Gift from Nature" *Journal of the Chinese Nutrition Society* 18:1–11.

Ulubelen, A. et al. (1989) "Constituents of *Achillea Spirokensis*" *Fitoterapia* 60(1): 93–94.

78–90408A & JP 53 127 842 Nov. 1978.

90–379459 & JP 2 273 622 Nov. 1990.

Nakatani et al. *Kagoshima Daigaku Rigakubu Kiyo, Sugaku, Butsurigaku, Kagaku*, vol. 23: 153–157, (1990). (Abstract Only).

Sugano and Akimoto, (1993), "Sesamin: A Multifunctional Gift From Nature", *Journal of Chinese Nutrition Society*, vol. 18, pp. 1–11.

Shimizu et al., (1993), "Studies on Desaturase Inhibitors of Polyunsaturated Fatty Acid Biosynthesis", Eds: A. Sinclair and R. Gibson, *American Oil Chemists'Society*, pp. 37–41.

Hirose et al., (1991), "Inhibition of choloesterol absorption and synthesis in rats by sesamin", *Journal of Lipid Research*, vol. 32, pp. 629–638.

Shimizu et al., (1991), "Sesamin Is a Potent and Specific Inhibitor of $\Delta 5$ Desaturase in Polyunsaturated Fatty Acid Biosynthesis", *Lipids*, vol. 26, No. 7, pp. 512–516.

Salerno et al., (1991), "The Use of Sesame Oil and Other Vegetable Oils in the Inhibition of Human Colon Cancer Growth in Vitro", *Anticancer Research*, vol. 11, pp. 209–216.

Fink et al., (1990), "Laboratory Models of Sepsis and Septic Shock", *Journal of Surgical Research*, vol. 49, pp. 186–196.

Shimizu et al., (1989), "Production of Dihmo–$\gamma$–linolenic Acid by *Mortierella alpina* 1S–4", *JAOCS*, vol. 66, No. 2, pp. 237–241.

Baker et al., (1983), "Evaluation of factors affecting mortality rate after sepsis in a murine cecal ligation and puncture model", *Surgery*, vol. Aug. 1983, pp. 331–335.

*Primary Examiner*—John Kight
*Assistant Examiner*—Howard C. Lee
*Attorney, Agent, or Firm*—Lahive & Cockfield, LLP

[57] ABSTRACT

The uses of lignans of the sesamin family to treat infection and inflammation is disclosed. These lignans may be delivered enterally or parenterally and either in the form of sesame oil or in purified form. A total parenteral nutrition solution or dietary supplement are the preferred forms of administration.

13 Claims, No Drawings

ANTI-INFLAMMATORY AND INFECTION PROTECTIVE EFFECTS OF SESAMIN-BASED LIGNANS

This application is a continuation of application Ser. No. 08/201,682 filed on Feb. 25, 1994 Entitled: ANTI-INFLAMMATORY AND INFECTION PROTECTIVE EFFECTS OF SESAMIN-BASED LIGNANS. The contents of all of the aforementioned applications are expressly incorporated by reference.

BACKGROUND OF THE INVENTION

The present invention relates to the formulation and use of dietary supplements and nutritional solutions for enteral and parenteral treatment of the effects of infection. These same dietary supplements or nutritional solutions may also be used as anti-inflammatory agents. The active ingredient in the dietary supplement or nutritional solution is a lignan of the sesamin family. This same active ingredient has particular effectiveness in total parenteral nutrition solutions to provide similar benefits.

The last decade has seen an explosion in the exploration of the interaction between diet and disease. In particular, the effects of various amino acids and lipids in the diet on a variety of conditions including heart disease, hypercatabolic states, liver disease, immunosupresssion, and infection treatment have been uncovered. Often, the effects are far removed from the norm and as such are unexpected. One of the most important developments of this type has been the discovery that by changing the dietary lipid content, positive effects in health treatment beyond plasma fat modification could be achieved. While the early work in modifying lipid content and type in diet came from an understanding that saturated fats cause particular problems in heart disease, later work determined that not just the use of polyunsaturated fats but also the type of polyunsaturated fat was important.

There are three major families of polyunsaturated fatty acids: $\omega 3$, $\omega 6$ and $\omega 9$. The names are based on location of the closest double bonds to the methyl end of the fatty acid; that is, if the closest double bond is between the third and fourth carbon atoms from the methyl group, the molecule is classified as an $\omega 3$ fatty acid while if the double bond is between the 6th and 7th carbon atoms, it is classified as an $\omega 6$ fatty acid. Mammals can desaturate or elongate fatty acid chains but cannot interconvert fatty acids from one family to another. The most important dietary fatty acids are the $C_{18}$ and $C_{20}$ fatty acids, primarily linoleic (C18:2$\omega$6), linolenic acid (C18:3$\omega$3) and dihomo-$\gamma$-linolenic acid (C18:3$\omega$6). Manipulation of the content of these fatty acids changes the arachidonic eicosapentanoic and docosahexanoic acid (C20:4$\omega$6, C20:5$\omega$3, and C22:6$\omega$ receptively) ratios and can cause far reaching effects in terms of immunosuppression, response to hypercatabolic states, and infection. For example, U.S. Pat. No. 4,752,618, issued Jun. 21, 1988, on an application of Mascioli et al., the disclosure of which is incorporated herein by reference, discloses the beneficial effects of $\omega 3$ fatty acids in the treatment of infection. In U.S. Pat. No. 5,260,336, issued Nov. 3, 1993, on an application of Forse et al., the disclosure of which is also incorporated herein by reference, concerns a method of minimizing the effect of catabolic illness or infection using an oil such as oleic acid which is rich in $\omega 9$ fatty acids. Other similar patents and articles, such as U.S. Pat. No. 4,810,726, issued Mar. 7, 1989, on an application of Bistrian et al., the disclosure of which is also incorporated herein by reference, disclose other means of treating illness using fatty acid dietary manipulation.

The "culprit" in many diets appears to be the high level of $\omega 6$ fatty acids, primarily linoleic acid, a precursor for the formation of arachidonic acid which is a substrate for the production of proinflamatory dienoic eicosanoids including $PGE_2$ and $TxA_2$ which can lead to elevated levels of thromboxane $A_2$ and related prostanoids. Elevation of these prostanoids has been linked to problems in response to endotoxin challenge and other infection states. Accordingly, the new wave in diets has been to minimize the $\omega 6$ fatty acid content (which, although an essential fatty acid, is not needed in the quantities found in most commercial oils) while maximizing the $\omega 3$ fatty acids (e.g., fish oil) and $\omega 9$ fatty acids (e.g., canola oil).

One byproduct of the recent exploration of the relationship between dietary modification and health has been a renewed look at traditional homeopathic remedies. One of these is sesame oil, which has long been known as a traditional health or medicinal food. Recent studies of sesame oil, which contains primarily $\omega 6$ fatty acids, indicate that the health benefits from use of sesame oil is based not on the fatty acid content, but rather on a lignan included therein, sesamin. In fact, sesamin is but one of several related lignans found in sesame oil. These lignans include sesaminol, sesamolin, episesamin and episesaminol. A recent article entitled "Sesamin: A Multifunctional Gift From Nature", by M. Sugano and K. Akimoto, *Journal of Chinese Nutrition Society* 18, 1–11 (1993), is a summary of known and projected effects of sesamin. This article suggests that the possible benefit of sesamin arise from its interference with linoleic acid metabolism, hypothesizing that the methodology is with interference with $\delta$-5-desaturate, an enzyme that catabolizes the reaction from dihomo-$\gamma$-linolenic acid (DGLA) to arachidonic acid (AA), an important step in linoleic acid metabolism. The article also cites other papers discussing other possible beneficial effects of sesamin including hypocholesterolemic action, enhancement of hepatic detoxification of chemicals and alcohol, a protective effect against chemically induced mammary cancer, in vivo antioxidative action and more problematic, a potential link to immunopotentiation.

Although this list of possible beneficial effects of sesamin and its related lignans is impressive, nothing has been said or discussed on its possible effects on infection and/or inflammation. In fact, if the mechanism of action hypothesized is correct, i.e., affecting $\delta$-5-desaturase, feedback inhibition might turn off this anti-infective activity and there would be no basis for any inflammatory activity. As is disclosed herein, there is now reason to believe that this proposed mode of operation is incorrect, and that the actual means of activity of sesamin and its related lignans is on either phospholipase $A_2$ or cyclooxygenase. Either of these mechanisms could cause anti-inflammatory effects. It should be noted, however, that identifying the mode of operation is not required to practice the invention.

Accordingly, an object of the invention is to treat infection and those at risk with infection with a dietary supplement or nutrition solution which provides added health benefits.

A further object of the invention is to provide a dietary supplement or nutrition solution, e.g., a parenteral nutrition solution, which provides anti-inflammatory activity.

Another object of the invention is to provide a parenteral nutrition solution, preferably a total parenteral nutrition solution, which has both anti-inflammatory and anti-infection characteristics.

These and other objects and features of the invention will be apparent from the following description and the claims.

SUMMARY OF THE INVENTION

The present invention features a method of treating infection and inflammation as well as dietary supplements and parenteral nutrition solutions useful in the methods of the invention. These dietary supplements and parenteral nutrition solutions have lignans in the sesamin family as the active ingredient.

More particularly, the present invention concerns a method of treating infection and minimizing the possibility of infection in at risk persons by administering an effective amount of a lignan selected from the group consisting of sesamin, episesamin, sesaminol, sesamolin, episesaminol, and mixtures thereof. An "effective amount", as used herein, means an amount sufficient to show statistically significant anti-infection or anti-inflammatory effects. The range of effective amount is about 1–10 mg/kg body weight. These lignans can be administered in purified form, such as purified sesamin, or administered in the form of sesame oil. For certain uses, enteral administration in the form of a dietary supplement containing an effective amount of the lignan is preferred, while for others, parenteral administration may be preferred. The dietary supplement should include essential fatty acids and, possibly, essential vitamins and minerals in addition to lignan. In its most fulsome form, the parenteral nutrition solution may be used as a total parenteral solution, containing all essential nutrients for health. These same solutions may be used not just for treating infection but also for treating inflammation.

DETAILED DESCRIPTION OF THE INVENTION

The present invention is based on the beneficial effects of sesamin and its related lignans on treatment of infection and/or inflammation. As noted, the common hypothesis for all actions of sesamin described to date has been the theory that it affects the enzyme δ-5-desaturase. In contrast, it appears that this scientific theory may be wrong and that it appears instead to be that sesamin inhibits the activity of cyclooxygenase (an enzyme which converts arachidonic acid to its metabolites) or the activity of phospholipase $A_2$ (an enzyme which releases arachidonic acid from membrane phospholipids). As such, since drugs which inhibit the activity of phospholipase $A_2$ (such as aspirin and several steroids) or cyclooxygenase (such as indomethacin) have anti-inflammatory effects, it appears that sesamin and its related lignans could be used as anti-inflammatory agents. Further, as will be shown herein, direct testing shows that sesamin has surprising anti-infection capabilities.

The following non-limiting examples show the activity of these lignans in terms of lipid metabolism and infection treatment.

EXAMPLE 1

In this example, the effects of a sesame oil diet on circulating lipids and the mode of activity of the lignans is investigated.

More particularly, if, as has been postulated by others, sesamin inhibits δ-5-desaturase activity, it would be expected that a decrease in arachidonic acid levels would coincide with an accumulation of dihomo-γ-linoleic acid from the sesame oil diet. However, under this mode of operation, there should be no effect on $PGE_2$ or $TxB_2$ levels. In contrast, if the $PGE_2$ and $TxB_2$ values are modified, this would not support the δ-5-desaturase mode of activity but rather a cyclooxygenase or phospholipase $A_2$ activity mode.

In this and the following example, a comparison was made between two diets which were as close in fatty acid and nutritional content as possible except one contained sesame oil, and its associated sesamin lignans, while the other was based on safflower oil. Sesame oil (Welch, Holme & Clark Company, Inc., Newark, N.J.), and safflower oil (SVO Specialty Products, Culberton, Mont.), provided the ω6 fats. Palm oil and Trisum (high oleic sunflower oil) were used as fat fillers. Table 1 shows the fat portion of the diet.

TABLE 1

|     | Safflower Oil | Sesame Oil | Palm Oil | Trisum |
| --- | --- | --- | --- | --- |
| SO  | 52 g | 0    | 88 g | 10 g |
| SSO | 34 g | 34 g | 82 g | 0    |

The lipid portions of each diet were approximately equal in the amounts of saturated, monounsaturated and polyunsaturated fats (approximately 10% each) and also equal in the amount of linoleic acid.

One hundred fifty grams of the lipid was added to 850 g. of AIN-76 basel diet, a fat-free basel diet which contains essential minerals and vitamins. The diets each had 30% of the calorie value and 15% by weight formed from the oil. An antioxidant, t-butyl hydroxytoluene (0.05%) was added and the resulting diets were thoroughly mixed. The diets were prepared in bulk, partitioned into daily rations, and stored at 4° C.

Balb/c mice (Jackson Laboratories) were fed the diets ad libium for a period of three weeks. The animals were fed every day before dusk. The phospholipid fatty acid compositions of plasma and of the liver cell membranes were determined by gas chromatography following thin layer of chromatography. The results showed a 1–3% incorporation of DGLA into the phospholipids from both the plasma and liver cell membranes for those mice fed with the sesame oil diets while none was found in those fed with the safflower oil diets. In addition, ten animals of each group were injected with 10µ g/kg body weight lypopolysacchride which induces the production of proinflamatory mediators. Plasma samples were collected 90 minutes later, stored at −90° C., and used to determine if there were any effects on the concentration of the pro-inflammatory mediators, TNF-α, $PGE_2$ and $TxB_2$. These mediators decreased by approximately by 50% in the sesame oil diets when compared with the safflower oil diet.

The experimental determination of a marked decrease in $PGE_2$ and $TxB_2$ after sesame oil diet show what would be expected if cyclooxygenase or phospholipase $A_2$ were the affected enzymes. Thus, it appears that the mode of operation suggested by the prior articles is probably incorrect and the modes of operation proposed herein are correct. In addition, since the modes of operation now postulated (and confirmed by experiment) are the same as are shown for a variety of steroidal and other anti-inflammatory drugs such as aspirin or indomecithin, these lignans should have similar anti-inflammatory properties.

EXAMPLE 2

In this example, the same diets and mice were used to determine if diet modification had any effect on the ability of the animals to withstand infection. The animals were fed the diets for three weeks ad libium.

At the end of the three week feeding period, twenty animals in each group underwent cecal ligation and puncture. The mice were anaesthetized and then shaved over the anterior abdominal wall. A midline incision approximately 2 cm long was made, sufficient to expose the cecum and adjoining intestine. With a 3-0 silk suture, the cecum was tightly ligated at its base without causing bowel obstruction. The cecum was then punctured twice with a 22 gauge needle, gently squeezed to exude feces and to ensure that the two puncture holes did not close. The overlapping abdominal incision was then closed and 1 ml of saline was administered subcutaneously for fluid resuscitation. This cecal ligation and puncture is a widely accepted form of infection model to resemble abdominal sepsis. See, e.g., C. Baker et al., "Evaluation of factors affecting mortality rate after sepsis in a murine cecal ligation and puncture model," *Surgery*(Aug. 1983), 331–335. Survival of the mice is the normal measure of treatment effectiveness.

Thirteen of the twenty mice in the group maintained on the sesame oil diet survived (65%) while only four of the twenty mice in the safflower oil diet survived (20%). Using a student t-test, the mortality rates were significantly different ($p<0.01$). Accordingly, it is clear that not only does a diet including sesamin reduce the levels of inflammatory molecules such as TNF-$\alpha$, $PGE_2$ and $TxB_2$ but it also provides protection against infection.

Those skilled in the art will recognize other alternative forms of the invention besides those disclosed in the above examples. There examples are merely exemplary of the invention which is defined by the following claims.

What is claimed is:

1. A method of treating infection and minimizing the possibility of infection in at risk persons comprising administration of an effective amount of sesame oil to the at risk persons.

2. The method of claim 1 wherein said sesame oil is administered enterally.

3. The method of claim 2 wherein said enteral administration comprises administration of a dietary supplement containing an effective amount of said sesame oil.

4. The method of claim 3 wherein said dietary supplement further comprises essential vitamins and minerals.

5. The method of claim 1 wherein said sesame oil is administered parenterally.

6. The method of claim 5 wherein said parenteral administration comprises administration of said sesame oil as part of a total parenteral nutrition diet.

7. The method of claim 5 wherein said sesame oil is administered as part of an oil included in a parenteral diet.

8. A method for treating infection or protecting against infection associated with abdominal sepsis, comprising administering to an animal in need thereof an effective amount of sesame oil.

9. The method of claim 8, wherein said sesame oil is administered enterally.

10. The method of claim 8, wherein said enteral administration comprises administration of a dietary supplement containing an effective amount of said sesame oil.

11. The method of claim 10, wherein said dietary supplement further comprises essential vitamins and minerals.

12. The method of claim 8, wherein said sesame oil is administered parenterally.

13. The method of claim 8, wherein said parenteral administration comprises administration of said sesame oil as part of a total parenteral nutrition diet.

* * * * *